United States Patent [19]
Lindsay

[11] Patent Number: 5,810,840
[45] Date of Patent: Sep. 22, 1998

[54] VACUUM EXTRACTOR

[76] Inventor: Richard G. Lindsay, 6824 Elk Canyon Rd., Oklahoma City, Okla. 73162

[21] Appl. No.: 869,860

[22] Filed: Jun. 5, 1997

Related U.S. Application Data

[63] Continuation-in-part of Ser. No. 782,996, Jan. 14, 1997, Pat. No. 5,713,909.

[51] Int. Cl.$^6$ .................................................. A61B 17/42
[52] U.S. Cl. .......................... 606/123; 606/122; 606/149
[58] Field of Search ................................. 606/122, 123, 606/124, 121, 119; 604/149

[56] References Cited

U.S. PATENT DOCUMENTS

| | | |
|---|---|---|
| 667,447 | 2/1901 | Miller . |
| 1,058,330 | 4/1913 | Page et al. . |
| 1,071,931 | 9/1913 | Long . |
| 2,702,038 | 2/1955 | Uddenberg et al. ................. 128/361 |
| 3,202,152 | 8/1965 | Wood et al. ........................ 128/361 |
| 5,019,086 | 5/1991 | Neward ............................. 606/123 |
| 5,163,944 | 11/1992 | Neward ............................. 606/123 |
| 5,281,229 | 1/1994 | Neward ............................. 606/123 |
| 5,569,265 | 10/1996 | Elliott .............................. 606/122 |

OTHER PUBLICATIONS

"Soft–cup vacuum extractors safely assist normal deliveries," Frank R. Witter, MD, *Contemporary OB/GYN*, not dated, pp. 3–8.

"Instrumental delivery in the 1990s: a commentary," David Acker, MD, *Contemporary OB/GYN*, ©1985 and 1990, pp. 9–10.

*Primary Examiner*—Michael Powell Buiz
*Assistant Examiner*—Julian W. Woo
*Attorney, Agent, or Firm*—Dunlap & Codding, P.C.

[57] ABSTRACT

A vacuum extractor for extracting a fetus from a birth canal during childbirth is provided. The vacuum extractor includes a cup, a substantially rigid stem, and a handle. The cup is provided with a flexible closed top end to enable the stem to be selectively moved from an operational position wherein the stem extends from the closed top end of the cup in substantial axial alignment with a vertical axis of the cup to an insertion position wherein the stem is angularly disposed relative to the vertical axis of the cup and a portion of the stem is recessed into the flexible closed top end of the cup to permit insertion of the cup into the birth canal. The handle has a first end, a second end, and a passageway extending therethrough from the first end to the second end. The handle is connected to the stem such that the first and second ends of the handle extend substantially laterally from the stem and the passageway of the handle in fluid communication with the vacuum cup. The first end of the handle is adapted to be connected to a vacuum source, and the second end is adapted to receive a vacuum release valve.

16 Claims, 6 Drawing Sheets

VACUUM EXTRACTOR

CROSS-REFERENCE TO RELATED APPLICATIONS

This application is a Continuation-In-Part of U.S. Ser. No. 08/782,996, filed Jan. 14, 1997, now U.S. Pat. No. 5,173,909 issued Feb. 3, 1998, entitled VACUUM EXTRACTOR.

STATEMENT REGARDING FEDERALLY SPONSORED RESEARCH OR DEVELOPMENT

Not applicable.

BACKGROUND OF THE INVENTION

1. Field of the Invention

The present invention relates generally to obstetric extraction devices, and more particularly, but not by way of limitation, to an improved vacuum extractor having a cup with a flexible top end adapted to receive a portion of a stem so as to reduce the height of the vertical profile of the apparatus during introduction of the apparatus into a birth canal.

2. Description of Related Art

Many devices are known for assisting a physician in the extraction of a fetus from the birth canal during childbirth. Some of the devices include forceps and vacuum extractors. While each of these types of devices have been used successfully in the childbirthing process, problems in the use of each of these types of devices have nevertheless been experienced.

For example, the use of forceps has been known to cause severe injuries, in particular head injuries, to new born children. Also, due to the awkward shape of forceps, their use can cause discomfort and result in possible injury to the mother. In an effort to overcome the inherent problems associated with the use of forceps, vacuum extraction devices have been employed.

Vacuum extractors utilize a cup, the opening of which is applied to the fetal head after the device has been introduced into the birth canal. The cup is attached to a vacuum source to create a vacuum in the cup and thus adhere the cup to the fetal head. With the vacuum extractor adhered to the fetal head, the fetus can then be pulled from the birth canal by manipulating a handle provided on the end of the vacuum extractor.

A problem experienced with the use of vacuum extractors is their susceptibility to release from or "pop off" the fetal head. When a vacuum extractor repeatedly releases from a fetal head, the delivery time is increased and the opportunity for the infliction of fetal scalp abrasions is increased.

Many "pop offs" result from a loss of vacuum pressure to the vacuum extractor due to an interruption of the vacuum to the vacuum extractor. This is due in large part to the fact that the prior art vacuum extractors are adapted to be connected to a vacuum source via a vacuum hose that is attached to the vacuum extractor at a point above the handle of the vacuum extractor along the longitudinal axis of the stem. In this location, the end of the vacuum hose is caused to be positioned in the palm of a physician's hand when the physician grips the handle of the vacuum extractor. As a consequence, the ability of the physician to comfortably grasp the vacuum extractor is interfered with, and more significantly, the potential exists for the vacuum hose to be bent or crimped by the physician's hand, thereby causing the vacuum pressure to the vacuum extractor to be inadvertently interrupted.

Also, for safety purposes, it is desirable when employing a vacuum extractor with certain types of vacuum units that the physician have the ability to immediately reduce or release the vacuum formed in the vacuum extractor. In an attempt to provide this ability, a vacuum release valve has been interposed between the vacuum extractor and the vacuum hose. However, due to the problem with the configuration of the prior art vacuum extractors discussed above, the release valve is caused to be located in the palm of a physician's hand when the physician grips the handle of the vacuum extractor, and thus is difficult for a physician to operate in an efficient manner.

To this end, a need has long existed for an improved vacuum extractor that is adpted to be easily introduced into the birth canal and that has a handle which can be grasped without interfering with the vacuum hose and which is adapted to receive a vacuum release valve wherein the vacuum release valve is efficiently and conveniently located on the vacuum extractor. It is to such an improved vacuum extractor that the present invention is directed.

BRIEF SUMMARY OF THE INVENTION

The present invention is directed to a vacuum extractor for extracting a fetus from a birth canal during childbirth. The vacuum extractor includes a cup, a stem, and a handle. The cup has a flexible top end, a sidewall, an open bottom end, and a height which extends from the open bottom end to the flexible top end and which permits insertion of the cup into the birth canal in a direction substantially perpendicular to a vertical axis of the cup.

The stem is substantially rigid and has a first end, a second end adapted to be connected to a vacuum source, and a passageway extending through the stem from the first end to the second end, the first end of the stem connected to the flexible top end of the cup such that the passageway of the stem is in fluid communication with the open bottom end of the cup. The flexible top end of the cup enables the stem to be selectively moved between an operational position wherein the stem extends from the top end of the cup in substantial axial alignment with the vertical axis of the cup and an insertion position wherein the stem is angularly disposed relative to the vertical axis of the cup and a portion of the stem is recessed into the flexible closed top end of the cup to permit insertion of the cup into the birth canal.

The handle has a first end, a second end, and a passageway extending therethrough from the first end to the second end. The handle is connected to the stem such that the first and second ends of the handle extend substantially laterally from the stem and the passageway of the handle is in fluid communication with the vacuum cup. The first end of the handle is adapted to be connected to a vacuum source, and the second end is adapted to receive a vacuum release valve.

The objects, features and advantages of the present invention will become apparent from the following detailed description when read in conjunction with the accompanying drawings and appended claims.

DETAILED DESCRIPTION OF THE INVENTION

Figures 1, 2:
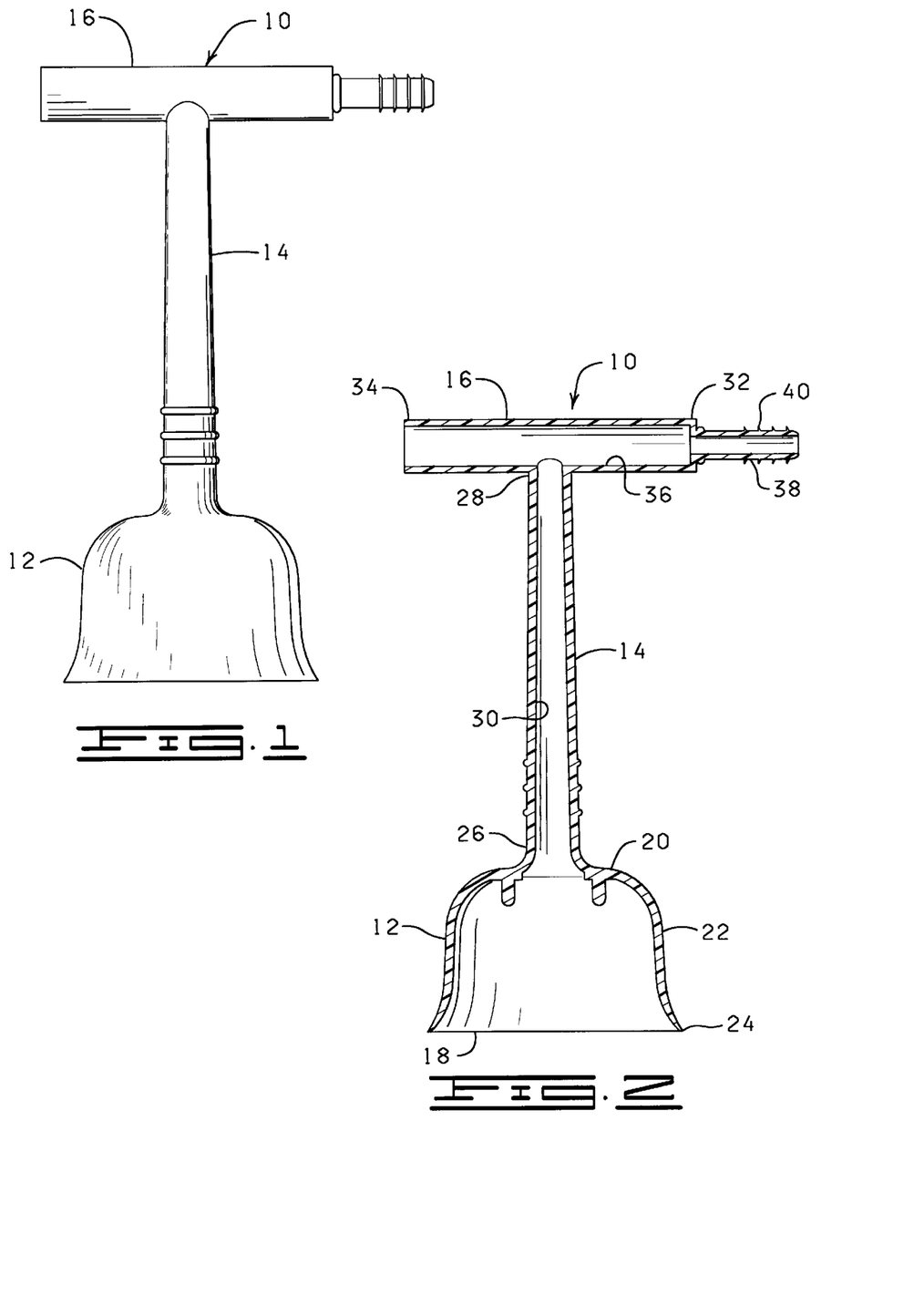
FIG. 1 is an elevational view of a vacuum extractor constructed in accordance with the present invention.
FIG. 2 is a cross sectional view of the vacuum extractor of FIG. 1.

Referring now to the drawings, and more particularly to FIGS. 1 and 2, a vacuum extractor 10 constructed in accordance with the present invention is illustrated. The vacuum extractor 10 includes a cup 12, a tubular stem 14, and a tubular handle 16. The vacuum extractor 10 is integrally formed from a suitable polymeric material, such as a virgin polyethylene, and by any suitable process, such as a conventional injection mold process which is well known to those of ordinary skill in the art.

The cup 12 is characterized as having an open bottom end 18, a top end 20, and a sidewall 22. The cup 12 is shown to be substantially bell-shaped and as having a thin flexible outer edge 24 to facilitate the formation of a seal between the cup 12 and a fetal head. However, it will be appreciated by those of ordinary skill in the art that the cup 12 may be formed into a variety of different configurations so long as the outer edge of the cup and a fetal head are able to conform with one another so that a seal may be formed in the cup to adhere the cup to the fetal head.

The stem 14 is elongated and has a first end 26, a second end 28, and a passageway 30 extending therethrough from the first end 26 to the second end 28. The first end 26 of the stem 14 is connected to the top end 20 of the cup 12 such that the passageway 30 of the stem 14 is in fluid communication with the open bottom end 18 of the cup 12.

Similar to the stem 14, the handle 16 has a first end 32, a diametrically opposed second end 34, and a passageway 36 extending therethrough from the first end 32 to the second end 34. The handle 16 is connected to the second end 28 of the stem 14 with the first end 32 and the second end 34 of the handle 16 extending laterally from the second end 28 of the stem 14 whereby the handle 16 and the stem 14 are arranged in a substantially T-shaped configuration. The handle 16 is further connected to the second end 28 of the stem 14 such that the passageway 36 of the handle 16 is in fluid communication with the passageway 30 of the stem 14, and thus, the passageway 36 of the handle 16 and the passageway 30 of the stem 14 are arranged in a substantially T-shaped configuration.

Figure 4:
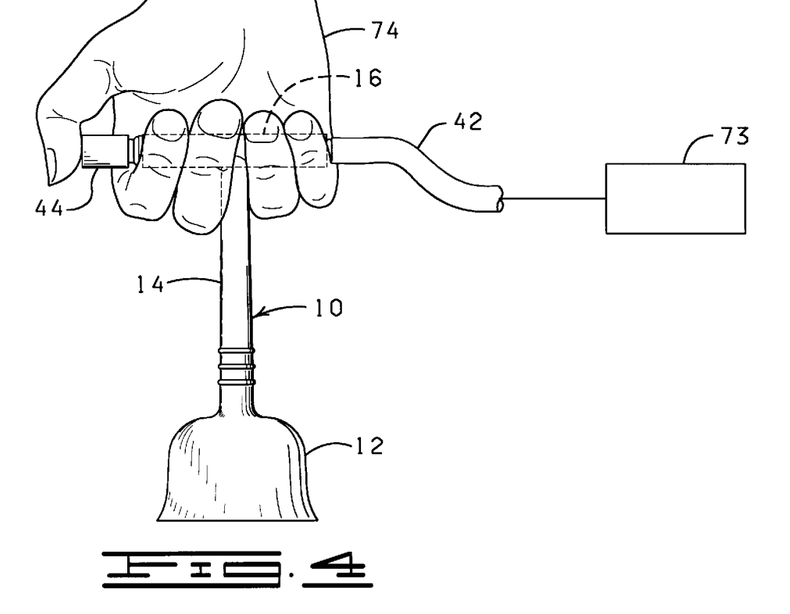
FIG. 4 is an elevational view of the vacuum extractor of the present invention illustrating the vacuum release valve connected to one end of the handle, a vacuum hose connected to the other end of the handle, and an individual gripping the handle.

The first end 32 of the handle 16 is configured to have a narrowed hose connector 38 which has a plurality of retaining ribs 40 for facilitating the connection of a vacuum hose 42 to the vacuum extractor 10, as illustrated in FIG. 4. The second end 34 of the handle 16 is adapted to receive a vacuum release valve as will be discussed in detail below. It will be appreciated, however, that the shape and size of both the first and second ends of the handle can be varied to receive a variety of different types of vacuum hoses and valves.

Figure 3A:
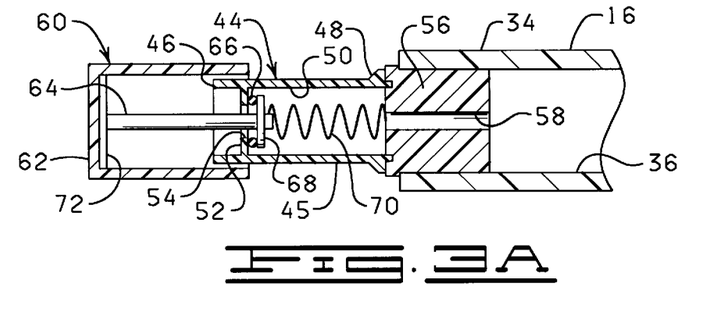
FIG. 3A is an enlarged cross sectional view of the second end of the handle shown with a vacuum release valve connected thereto and in a closed position.
Figure 3B:
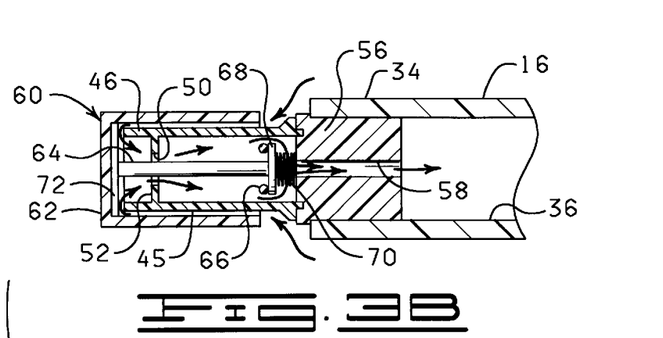
FIG. 3B is an enlarged cross sectional view of the second end of the handle shown with the vacuum release valve connected thereto and in an open position.

When it is necessary that a user of the vacuum extractor 10 be able to quickly release the vacuum formed in the vacuum extractor 10, a vacuum release valve 44 is connected to the second end 34 of the handle 16. A suitable valve is illustrated in FIGS. 3A and 3B. The valve 44 includes a valve body 45 having a first end 46, a second end 48, and a passageway 50 extending therethrough from the first end 46 to the second end 48. The valve body 45 further has an interior shoulder 52 with a central opening 54.

The first end 46 of the valve body 45 is connected to a handle adaptor member 56 which is shaped to be received in the second end 34 of the handle 16, as substantially shown in FIGS. 3A and 3B. It will be appreciated, however, that the handle adaptor member 56 can also be shaped to fit over the second end 34 of the handle 16 as opposed to fitting within the second end 34 of the handle 16. The handle adaptor member 56 has a centrally disposed flow passage 58 extending therethrough so as to establish fluid communication between the passageway 36 of the handle 16 and the passageway 50 of the valve body 45 when the valve 44 is connected to the second end 34 of the handle 16. The valve body 45 is connected to the handle adaptor member 56 by any suitable fashion, such as by sonic welding.

To selectively seal the central opening 54 of the valve body 45 from the passage 58 of the handle adaptor member 56, a push button assembly 60 is provided. The push button assembly 60 includes a button 62, a shaft 64, and a seal ring 66. The shaft 64 is provided with a flange 68 for supporting the seal ring 66 on one side thereof and for engaging a spring 70 on the opposite side thereof. The shaft 64 is disposed through the central opening 54 of the valve body 45 with the seal ring 66 positioned between the interior shoulder 52 and the flange 68 of the shaft 64. The distal end of the shaft 64 is connected to a central portion of the button 62, which is configured to extend over the second end 48 of the valve body 45.

The spring 70 is disposed between the handle adaptor member 56 and the flange 68 of the shaft 64 such that one end of the spring 70 engages the handle adaptor member 56 and the other end of the spring 70 engages the flange 68 of the shaft 64. In a closed position, illustrated in FIG. 3A, the spring 70 biases the flange 68 toward the interior shoulder 52 of the valve body 45 so as to cause the seal ring 66 to form a seal between the interior shoulder 52 and the flange 68. In an open position, illustrated in FIG. 3B, the flange 68 is forced away from the interior shoulder 52 by pushing on the button 62 thereby breaking the seal between the interior shoulder 52 and the flange 68. In the open position, air is able to flow through the flow passage 58 of the handle adaptor member 56, through the central opening 54 of the valve body 45, and between the second end 48 of the valve body 45 and the button 62, thereby releasing a vacuum formed in the cup 12.

To prevent the button 62 from forming a seal with the second end 48 of the valve body 45 when the button 62 is pushed, the button 62 is provided with a support rib 72. The rib 72 extends downwardly from the bottom side of the button 62 so as to engage the second end 48 of the valve body 45 when the button 62 is pushed thereby maintaining a flow path between the second end 48 of the valve body 45 and the button 62 when the release valve 44 is in the open position.

As mentioned above, FIG. 4 illustrates the vacuum extractor 10 with the vacuum hose 42 attached to the first end 32 of the handle 16. The vacuum hose 42 is diagrammatically illustrated as being connected to a vacuum source 73. FIG. 4 further illustrates the vacuum release valve 44 connected to the second end 34 of the handle 16 and an individual's hand 74 operably gripping the handle 16. It will be appreciated that the unique configuration of the handle 16 provides the advantage of enabling an individual to grip the handle 16 of the vacuum extractor 10 during delivery without being concerned about inadvertently interrupting the vacuum in the cup 12 by pinching or crimping the vacuum hose 42 in the palm of their hand. The unique configuration provides the further advantage of allowing the vacuum release valve 44 to be efficiently located so that the individual can quickly and easily operate the vacuum release valve 44 with their thumb without having to vary their grip of the handle 16.

Figure 5:
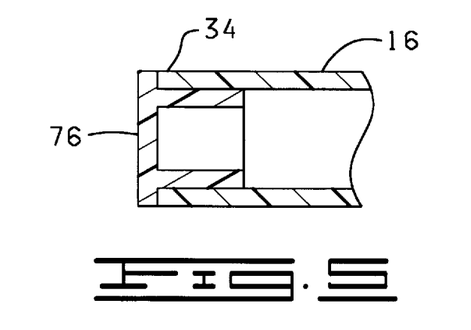
FIG. 5 is an enlarged cross sectional view of the second end of the handle with a plug disposed therein.

If the vacuum source to which the vacuum extractor 10 is being connected has a vacuum release, it may not be necessary to employ the valve 44. In those instances, the second end 34 of the handle 16 may be sealed with a plug 76, as illustrated in FIG. 5. The plug 76 is preferably dimensioned so that it may be press fitted in the second end 34 of the handle 16 and thus selectively removed therefrom. Alternatively, the plug 76 may be removably secured in the second end 34 of handle 16 with a suitable adhesive.

Figure 6:
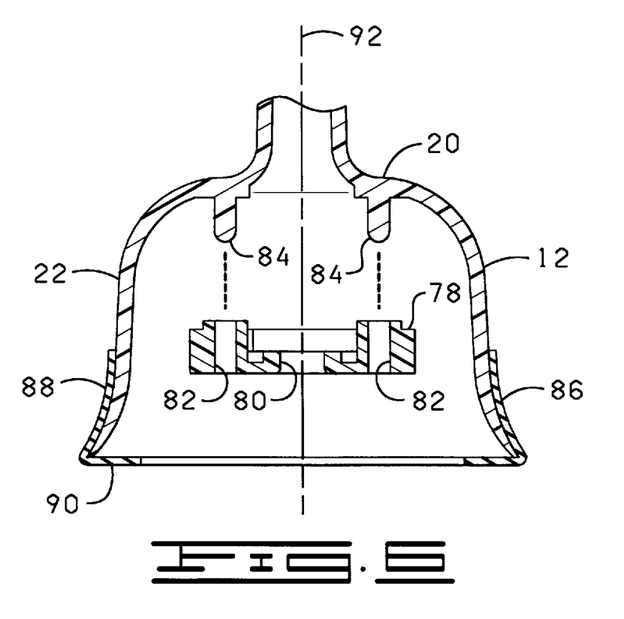
FIG. 6 is an enlarged cross sectional view of the cup illustrating a distributor disk and a protective sleeve.

Referring now to FIG. 6, a distributor disk 78 is provided in the cup 12 near the top end 20 thereof to limit the extent that the scalp of an infant may be drawn into the cup 12. The distributor disk 78 has a central opening 80 and a pair of openings 82. The openings 82 are sized to receive a pair of pegs 84 extending from the top end 20 of the cup 12. The distributor disk 78 is disposed on the pegs 84 such that the disk 78 is positioned in a spaced apart relationship relative to the top end 20 of the cup 12 and such that the outer edge of the disk 78 is spaced from the sidewall 22 of the cup 12 thereby providing a flow path around the disk 78. The disk 78 is secured to the pegs 84 by any suitable means, such as sonic welding.

To prevent the thin outer edge 24 of the cup 12 from cutting into the scalp of a fetus, a protective sleeve 86 can be positioned over the outer edge 24. The sleeve 86 has a first end portion 88 that is disposable about a lower portion of the sidewall 22 of the cup 12 and a second end portion 90 that is extendable radially inward over a portion of the bottom end 18 of the cup 12 in a substantially perpendicular relationship to a longitudinal axis 92 (FIG. 6) of the cup 12. The sleeve 86 is preferably formed from a soft, elastic material, such as rubber, so that the first end portion 88 of the sleeve 86 frictionally engages the sidewall 22 and the outer edge 24 of the cup 12 to retain the sleeve 86 on the cup 12 when the first end portion 88 of the sleeve 86 is disposed about the lower portion of the cup 12.

One of the advantages of using the sleeve 86 to cover the outer edge 24 of the cup 12, besides covering the outer edge 24 of the cup 12 with a soft, flexible layer of material, is that the sleeve 86 is positioned on the cup 12 such that the upper portion of the cup 12 is not covered. Thus, due to the translucent characteristics of virgin polyethylene, a physician is able to visually monitor how far into the cup 12 the fetal head has been drawn through the upper portion of the cup 12. Another notable advantage of the sleeve 86 is that by allowing the second end portion 90 of the sleeve 86 to extend radially inward over the open bottom end 18 of the cup 12, the second end portion 90 of the sleeve 86 is able to conform to the fetal head thereby providing a greater surface area with which the fetal head is in contact and aiding in preventing the cup 12 from sliding and rotating on the fetal head as a physician manipulates the vacuum extractor 10 during the delivery process.

Referring now to FIGS. 7–10, another embodiment of a vacuum extractor 100 constructed in accordance with the present invention is illustrated. The vacuum extractor 100 includes a cup 102, a stem 104, and a handle 106. The vacuum extractor 100 is integrally formed from a suitable polymeric material, such as a virgin polyethylene, and by any suitable process, such as a conventional injection mold process which is well known to those of ordinary skill in the art.

Figures 7, 8:
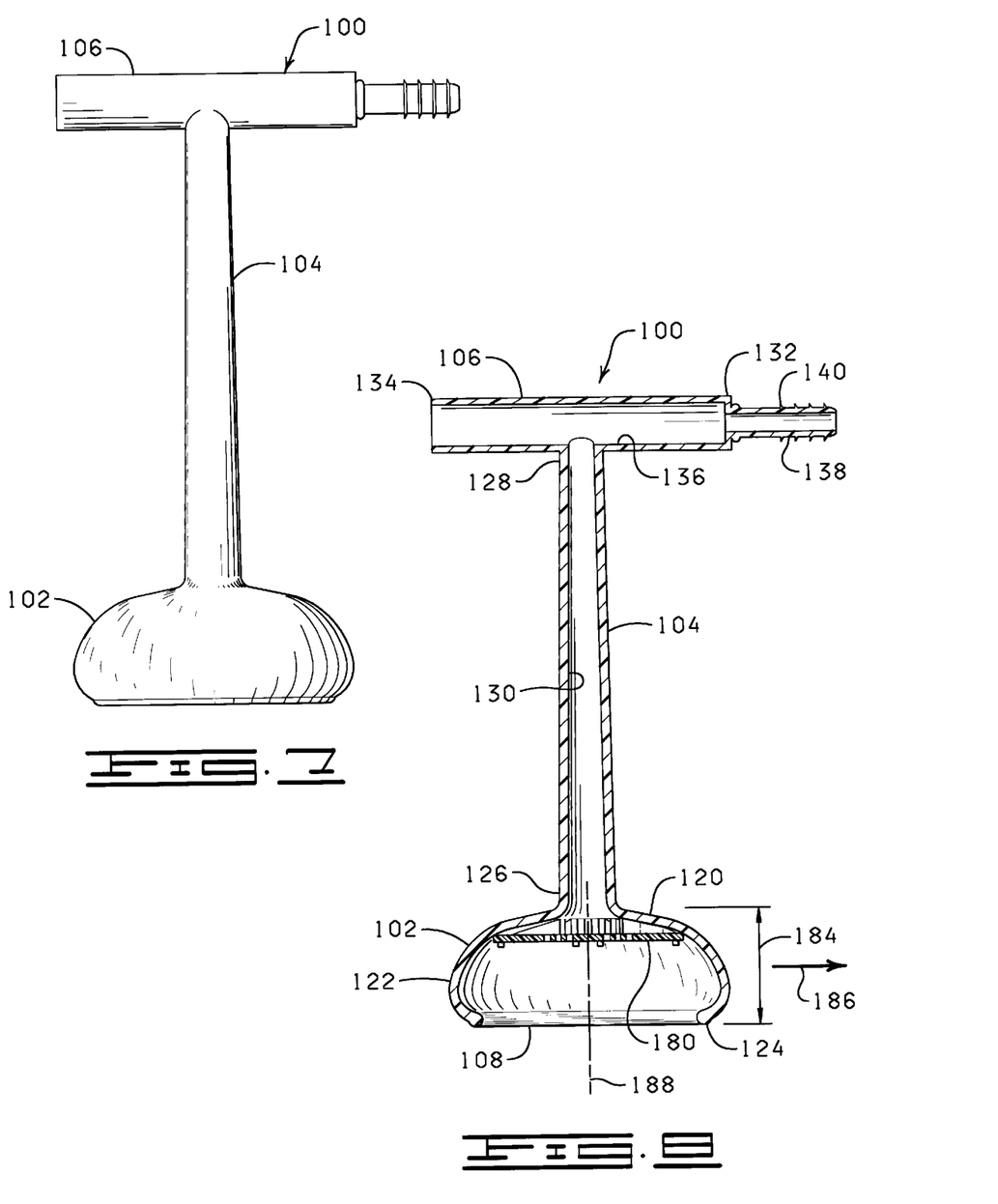
FIG. 7 is an elevational view of another vacuum extractor constructed in accordance with the present invention.
FIG. 8 is a cross sectional view of the vacuum extractor of FIG. 7 illustrated in an operational position.
Figure 8A:
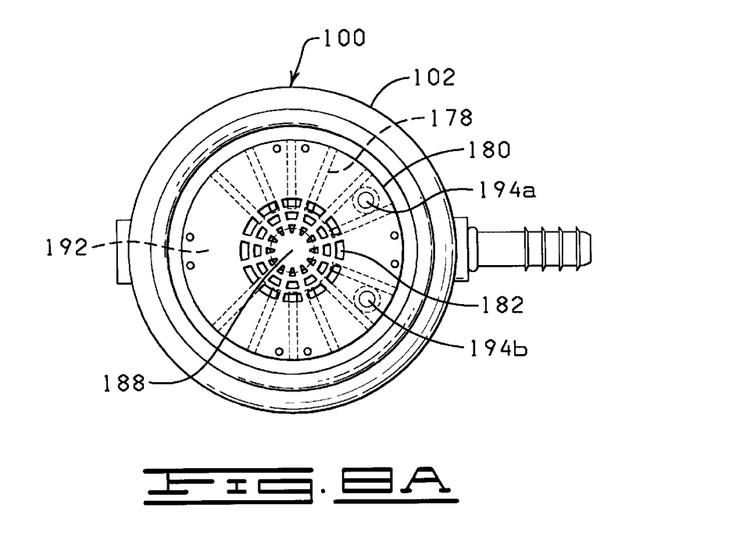
FIG. 8A is a bottom plan view of the vacuum extractor of FIG. 8.
Figure 9:
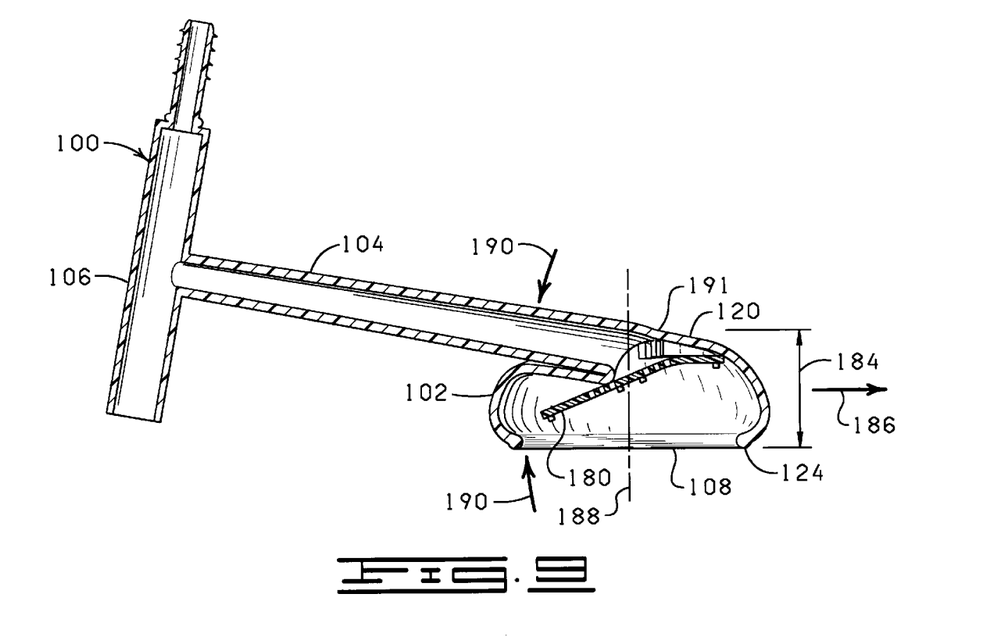
FIG. 9 is a cross sectional view of the vacuum extractor of FIG. 7 illustrated in an insertion position.

The cup 102 is characterized as having an open bottom end 108, an flexible closed top end 120, an outwardly rounded sidewall 122 and a rim 124 having a smooth or rounded configuration. The cup 102 is shown to be substantially mushroom-shaped whereby the interior diameter of the sidewall 122 is greater than the interior diameter of the rim 124. The configuration of the rim 124 in cooperation with the mushroom shape of the cup 102 facilitate the formation of a seal between the cup 102 and a fetal head in a manner well known in the art.

The stem 104 has a first end 126, a second end 128, and a passageway 130 extending therethrough from the first end 126 to the second end 128. The first end 126 of the stem 104 is connected to the closed top end 120 of the cup 102 such that the passageway 130 of the stem 104 is in fluid communication with the open bottom end 108 of the cup 102.

The stem 104 is made to be substantially rigid along the length thereof so that the entire stem 104 may be moved relative to the cup 102 in a manner to be discussed in detail below without the stem 104 being significantly deformed during insertion of the vacuum extractor 100 into the birth canal or during use of the vacuum extractor 100 to aid in the extraction of an infant.

The handle 106 has a first end 132, a diametrically opposed second end 134, and a passageway 136 extending therethrough from the first end 132 to the second end 134. The handle 106 is connected to the second end 128 of the stem 104 with the first end 132 and the second end 134 of the handle 106 extending laterally from the second end 128 of the stem 104 whereby the handle 106 and the stem 104 are arranged in a substantially T-shaped configuration. The handle 106 is further connected to the second end 128 of the stem 104 such that the passageway 136 of the handle 106 is in fluid communication with the passageway 130 of the stem 104, and thus, the passageway 136 of the handle 106 and the passageway 130 of the stem 104 are arranged in a substantially T-shaped configuration.

Figure 10:
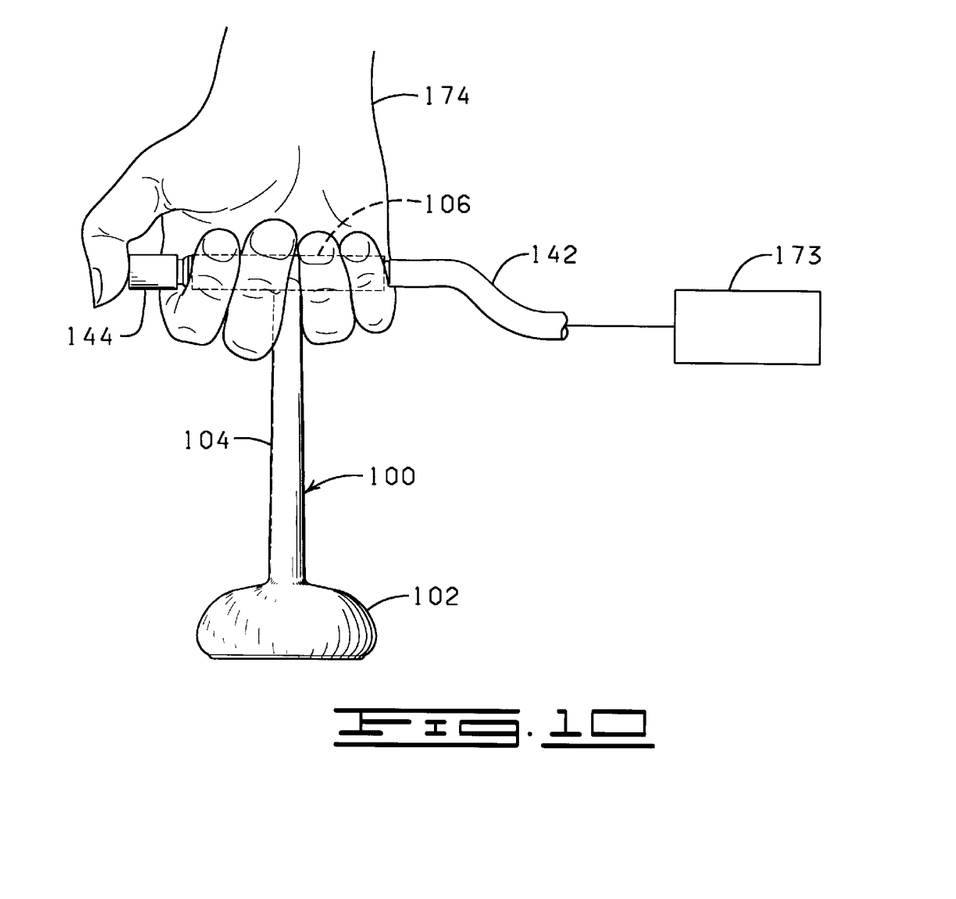
FIG. 10 is an elevational view of the vacuum extractor of FIG. 7 illustrating the vacuum release valve connected to one end of the handle, a vacuum hose connected to the other end of the handle, and an individual gripping the handle.

The first end 132 of the handle 106 is configured to have a narrowed hose connector 138 which has a plurality of retaining ribs 140 for facilitating the connection of a vacuum hose 142 to the vacuum extractor 100, as illustrated in FIG. 10. The second end 134 of the handle 106 is adapted to receive a vacuum release valve 144 (FIG. 10) so that a user of the vacuum extractor 100 is able to quickly release the vacuum formed in the vacuum extractor 100. The vacuum release valve 144 is constructed and operated in a manner identical to that described above in reference to the vacuum release valve 94. Therefore, for the sake of brevity, a detailed description of the vacuum release valve 144 will not be repeated.

FIG. 10 illustrates the vacuum extractor 100 with the vacuum hose 142 attached to the first end 132 of the handle 106. The vacuum hose 142 is diagrammatically illustrated as being connected to a vacuum source 173. FIG. 10 further illustrates the vacuum release valve 144 connected to the second end 134 of the handle 106 and an individual's hand 174 operably gripping the handle 106. It will be appreciated that the unique configuration of the handle 106 provides the advantage of enabling an individual to grip the handle 106 of the vacuum extractor 100 during delivery without being concerned about inadvertently interrupting the vacuum in the cup 102 by pinching or crimping the vacuum hose 142 in the palm of their hand. The unique configuration provides the further advantage of allowing the vacuum release valve 144 to be efficiently located so that the individual can quickly and easily operate the vacuum release valve 144 with their thumb without having to vary their grip of the handle 106.

If the vacuum source to which the vacuum extractor 100 is being connected has a vacuum release, it may not be necessary to employ the valve 144. In those instances, the second end 134 of the handle 106 may be sealed with a plug, such as plug 76 illustrated in FIG. 5.

Referring now to FIGS. 8, 8A, 9, and 9A, a plurality of radially spaced support ribs 178 are formed on the interior side of the cup 102 so as to extend radially along the closed top end 120 thereof. A distributor disk 180 is also provided in the cup 102 near the closed top end 120 thereof to limit the extent that the scalp of an infant may be drawn into the cup 102. The distributor disk 180 is provided with a plurality of flow openings 182.

The cup 102 has a height 184 extending from the open bottom end 108 to the closed top end 120 which is minimized to permit the cup 102 to be inserted into the birth canal in a direction (represented by arrow 186) which is substantially perpendicular to a vertical axis 188 of the cup 102. To facilitate insertion of the cup 102 into the birth canal, the construction of the cup 102 and the stem 104 permit the stem 104 to be folded relative to the cup 102 so that the stem 104 does not obstruct insertion of the cup 102 into the birth canal in the direction 186.

It should be appreciated by those of ordianary skill in the art that the vacuum extractor 100 is not limited in use to vaginal deliveries but may also be used in Cesarean deliveries. As such, it should be understood that the term "birth canal" as used herein includes the birthing passage formed by the cervix, vagina, and vulva, as well as the birthing passage formed by surgical incision of the walls of the abdomen and uterus.

FIG. 8 illustrates the stem 104 in an operational position, and FIG. 9 illustrates the stem 104 in an insertion position. In the operational position, the stem 104 extends from the closed top end 120 of the cup 102 in substantial axial alignment with the vertical axis 188 of the cup 102 so that a physician may pull an infant from the birth canal by manipulation of the handle 106 when the cup 102 is held onto the infant's head by a vacuum created in the cup 102. In the insertion position, the stem 104 is angularly disposed relative to the vertical axis 188 of the cup 102 and a portion of the stem 104 is recessed into the flexible closed top end 120 of the cup 102 such that a combination of the stem 104 and the cup 102 has a vertical profile having a height substantially equal to the height 184 of the cup 102, thereby facilitating insertion of the cup 102 into the birth canal in the direction 186. The rigidity of the stem 104 and the flexibility of the closed top end 120 of the cup 102 enables the stem 104 to be selectively moved by application of a folding force (represented by arrows 190) on the stem 104 in the cup 102 from the operational position to the insertion position (depicted in FIGS. 9 and 9A). The closed top end 120 of the cup 102 is further constructed to be biased in the operational position so that upon insertion of the cup 102 into the birth canal and removal of the folding force 190, the cup 102 will return to the operational position (FIG. 8).

As the stem 104 is moved from the operational position to the insertion position, one side of the closed top end 120 of the cup 102 is caused to collapse inwardly and the opposing side of the closed top end 120 of the cup 102 is caused to extend. It should be appreciated that by constructing the stem 104 and the closed top end 120 of the cup 102 such that one side of the closed top end 120 of the cup 102 collapses and the opposing side extends, the transition between the stem 104 and the closed top end 120 of the cup 102 along the leading side of the cup 102, as designated by the reference numeral 191 in FIG. 9, is caused to be relatively smooth so that no portion of the stem 104 poses a significant obstruction to insertion of the cup 102 into the birth canal. It should be further appreciated that the substantial rigidity of the stem 104 results in the passageway 130 of the stem 104 remaining substantially undistorted along the length thereof in both the operational position and the insertion position so as not to reduce or interrupt the vacuum in the cup 102.

To facilitate positioning of the stem 104 in the insertion position, an area 192 of increased flexibility may be formed on the closed top end 120 of the cup 102 by spacing a pair of adjacent support ribs 178 at an angle of approximately 60° to 90° whereby the spaced apart ribs 178 are spaced apart a distance approximately equal to or greater than the diameter of the stem 104. The area 192 of increased flexibility enables the closed top end 120 of the cup 102 to more easily conform to the contour of the stem 104 when the stem 104 is in the insertion position without significantly diminishing the integrity of the closed top end 120 of the cup 102.

Figure 9A:
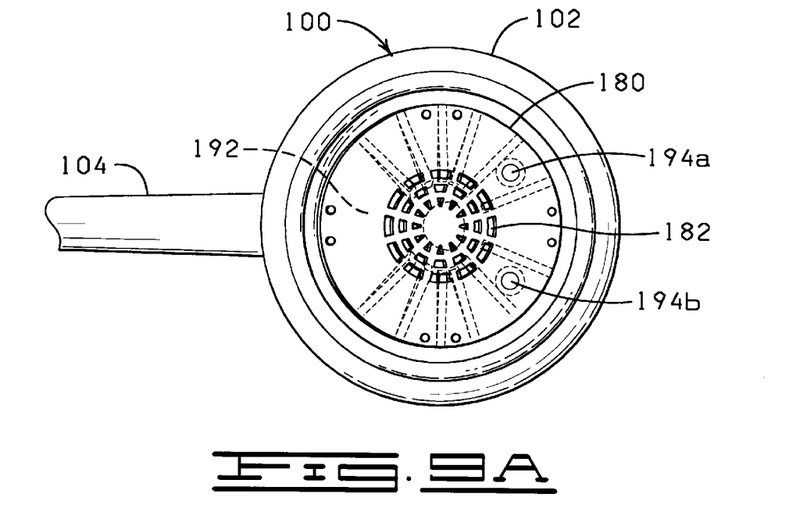
FIG. 9A is a bottom plan view of the vacuum extractor of FIG. 9.

To further facilitate positioning of the stem 104 in the insertion position, the distributor disk 180 is connected to the interior side of the closed top end 120 of the cup 102 at two radially spaced connection points 194a and 194b which are preferably symmetrically positioned in a diametrically opposed relationship relative to the support ribs 178 defining the area 192 of increased flexibility so that the free end of the distributor disk 180 is positioned adjacent to the the area 192 of increased flexibity. The connection points 194a and 194b are disposed at an angle of less than 180° relative to the vertical axis 188 of the cup 102, and more preferably at an angle of 60° to 120°. As shown in FIGS. 9 and 9A, connecting the distributor disk 180 to the cup 102 in this manner permits the free side of the distributor disk 180 to move freely within the cup 102 when the stem 104 is moved into the insertion position in a direction away from the connection points 194a and 194b so that the distributor disk 180 does not impede or restrict movement of the closed top end 120 of the cup 102 as the stem 104 is moved into the insertion position.

From the above description it is clear that the present invention is well adapted to carry out the objects and to attain the advantages mentioned herein as well as those inherent in the invention. While presently preferred embodiments of the invention have been described for purposes of this disclosure, it will be understood that numerous changes may be made which will readily suggest themselves to those skilled in the art and which are accomplished within the spirit of the invention disclosed and as defined in the appended claims.

What is claimed:

1. A vacuum extractor for extracting a fetus from a birth canal during childbirth, the vacuum extractor comprising:

a cup having a flexible closed top end, a sidewall, an open bottom end, and a height which extends from the open bottom end to the flexible closed top end and which permits insertion of the cup into the birth canal in a direction substantially perpendicular to a vertical axis of the cup; and a substantially rigid stem having a first end, a second end adapted to be connected to a vacuum source, and a passageway extending through the stem from the first end to the second end, the first end of the stem connected to the flexible closed top end of the cup such that the passageway of the stem is in fluid communication with the open bottom end of the cup, the stem selectively movable between an operational position wherein the stem extends from the closed top end of the cup in substantial axial alignment with the vertical axis of the cup and an insertion position wherein the stem is angularly disposed relative to the vertical axis of the cup and a portion of the stem is recessed into the flexible closed top end of the cup to permit insertion of the cup into the birth canal.

2. The vacuum extractor of claim 1 wherein the stem is recessed into the flexible closed top end of the cup such that a combination of the stem and the cup has a vertical profile having a height substantially equal to the height of the cup.

3. The vacuum extractor of claim 1 wherein the flexible closed top end of the cup is biased in the operational position.

4. The vacuum extractor of claim 1 wherein the closed top end of the cup has a plurality of radially spaced support ribs formed on the interior side of the cup, at least one pair of adjacent support ribs spaced apart at angle of about 60° to 90° to form an area on the closed top end of the cup of increased flexibility for receiving the stem when the stem is moved to the insertion position.

5. The vacuum extractor of claim 1 further comprising a distributor disk positioned in the cup and secured to the interior side of the closed top end of the cup for limiting the extent that the scalp of an infant may be drawn into the cup, the distributor disk connected to the interior side of the closed top end of the cup at at least two radially spaced points which are disposed at an angle of less than 180° relative to the vertical axis of the cup whereby the flexibility of the closed top end of the cup remains substantially unimpeded by the distributor disk when the stem is moved to the insertion position.

6. The vaccum extractor of claim 5 wherein the radially spaced points are positioned in a substantially diametrically opposed relationship to the area of increased flexibility.

7. The vacuum extractor of claim 6 wherein the angle between the radially spaced points is in a range of from about 60° to about 120°.

8. A vacuum extractor for extracting a fetus from a birth canal during childbirth, the vacuum extractor comprising:

a cup having a flexible closed top end, a sidewall, an open bottom end, and a height which extends from the open bottom end to the flexible closed top end and which permits insertion of the cup into the birth canal in a direction substantially perpendicular to a vertical axis of the cup; and a substantially rigid stem having a first end, a second end, and a passageway extending through the stem from the first end to the second end, the first end of the stem connected to the flexible closed top end of the cup such that the passageway of the stem is in fluid communication with the open bottom end of the cup, the stem selectively movable between an operational position wherein the stem extends from the closed top end of the cup in substantial axial alignment with the vertical axis of the cup and an insertion position wherein the stem is angularly disposed relative to the vertical axis of the cup and a portion of the stem is recessed into the flexible closed top end of the cup to permit insertion of the cup into the birth canal; and a handle having a first end, a second end, and a passageway extending therethrough from the first end, the handle connected to the second end of the stem with the first and second ends of the handle extending laterally from the second end of the stem and the passageway of the handle in fluid communication with the passageway of the stem, the first end of the handle connectable to a vacuum source.

9. The vacuum extractor of claim 8 wherein the stem is recessed into the flexible closed top end of the cup such that a combination of the stem and the cup has a vertical profile having a height substantially equal to the height of the cup.

10. The vacuum extractor of claim 8 wherein the flexible closed top end of the cup is biased in the operational position.

11. The vacuum extractor of claim 8 wherein the closed top end of the cup has a plurality of radially spaced support ribs formed on the interior side of the cup, at least one pair of adjacent support ribs spaced apart at angle of at least about 60° to 90° to form an area on the closed top end of the cup of increased flexibility for receiving the stem when the stem is moved to the insertion position.

12. The vacuum extractor of claim 8 further comprising a distributor disk positioned in the cup and secured to the interior side of the closed top end of the cup for limiting the extent that the scalp of an infant may be drawn into the cup, the distributor disk connected to the interior side of the closed top end of the cup at at least two radially spaced points which are disposed at an angle of less than 180° relative to the vertical axis of the cup whereby the flexibility of the closed top end of the cup remains substantially unimpeded by the distributor disk when the stem is moved to the insertion position.

13. The vaccum extractor of claim 12 wherein the radially spaced points are positioned in a substantially diametrically opposed relationship to the area of increased flexibility.

14. The vacuum extractor of claim 13 wherein the angle between the radially spaced points is in a range of from about 60° to about 120°.

15. The vacuum extractor of claim 8 wherein the passageway of the handle extends from the first end to the second end thereof, and wherein the vacuum extractor further comprises:

valve means connected to the second end of the handle for selectively releasing a vacuum formed in the cup.

16. The vacuum extractor of claim 15 wherein the first end of the handle is diametrically opposed from the second end of the handle.

* * * * *